United States Patent [19]

Sweeny et al.

[11] Patent Number: 4,720,417

[45] Date of Patent: Jan. 19, 1988

[54] FRAGRANCE-RELEASING PULL-APART SHEET

[75] Inventors: Norman P. Sweeny, North Oaks, Minn.; Jack W. Charbonneau, Somerset, Wis.; Orville F. Wienke, St. Paul, Minn.

[73] Assignee: Minnesota Mining and Manufacturing Company, St. Paul, Minn.

[21] Appl. No.: 924,115

[22] Filed: Oct. 31, 1986

Related U.S. Application Data

[63] Continuation of Ser. No. 680,490, Dec. 11, 1984, abandoned.

[51] Int. Cl.⁴ .......................... A61L 9/04; B01J 13/00; D01F 1/02; D04H 1/04
[52] U.S. Cl. .................................... 428/201; 424/401; 424/451; 427/171; 428/204; 428/206; 428/207; 428/321.5; 428/323; 428/327; 428/402.2; 428/402.21; 428/402.22; 428/537.5; 428/905; 512/4

[58] Field of Search .................... 424/27, 37; 427/171; 428/201, 204, 206, 207, 321.5, 323, 327, 402.2, 402.21, 402.22, 537.5, 905

[56] References Cited

U.S. PATENT DOCUMENTS

| 3,516,941 | 6/1970 | Matson | 252/316 |
| 3,623,659 | 11/1971 | Maierson et al. | 239/56 |
| 4,186,743 | 2/1980 | Steiger | 128/294 |
| 4,487,801 | 12/1984 | Turnbull et al. | 428/313.5 |
| 4,528,226 | 7/1985 | Sweeny | 428/321.5 |

OTHER PUBLICATIONS

"Town and Country", Dec. 1984, p. 64.
"Scent Strip", Arcade Inc., 9/24/84.

Primary Examiner—Bruce H. Hess
Attorney, Agent, or Firm—Donald M. Sell; James A. Smith; Mark A. Litman

[57] ABSTRACT

Microencapsulated materials are released by rupturing of an adhesive layer on a substrate containing the capsules.

27 Claims, No Drawings

FRAGRANCE-RELEASING PULL-APART SHEET

This is a continuation of application Ser. No. 680,490 filed Dec. 11, 1984, now abandoned.

FIELD OF THE INVENTION

This invention relates to microencapsulated materials, articles containing microencapsulated materials and the method of preparing such articles. In particular, the present invention relates to microencapsulated materials adhesively secured between two temporarily adhered coated paper surfaces such that upon separation of said two surfaces, the capsules rupture, releasing material contained therein.

BACKGROUND OF THE INVENTION

Encapsulated materials have been used for many years in a wide variety of commercial applications. Early uses of encapsulated materials included paper coated with capsules bearing coloring material therein which could be used as a recording medium. U.S. Pat. No. 3,016,308 discloses one of the early efforts using encapsulated material as the image source on recording paper. U.S. Pat. Nos. 4,058,434 and 4,201,404 show other methods of application of encapsulated coloring materials on paper substrates to be used as imaging media and the like. U.S. Pat. No. 3,503,783 shows microcapsules having coloring material therein which are ruptureable by the application of heat, pressure and/or radiation because of a metal coating on the surface of the capsule. These ruptureable microcapsules, in one embodiment, may be secured between a substrate and a photoconductive top coat to enable photosensitive imaging of the system.

A wide variety of processes exist by which microcapsules can be manufactured. These varied processes provide different techniques for producing capsules of varying sizes, alternative material for the composition of the capsule shell and various different functional materials within the shell. Some of these various processes are shown in U.S. Pat. Nos. 3,516,846; 3,516,941; 3,778,383; 4,087,376; 4,089,802; 4,100,103 and 4,251,386 and British Patent Specification Nos. 1,156,725; 2,041,319 and 2,048,206. A wide variety of different materials may also be used in making the capsule shells. A popular material for shell formation is the polymerization reaction product between urea and formaldehyde or melamine and formaldehyde, or the polycondensation products of monomeric or low molecular weight polymers of dimethylolurea or methylolated urea with aldehydes. A variety of capsule forming materials are disclosed, for example, in U.S. Pat. Nos. 3,516,846 and 4,087,376 and U.K. Patent Specification Nos. 2,006,709 and 2,062,570.

As shown in these references, the principal utility of microencapsulated materials is in the formation of a surface coated with the microcapsules in a binder. The microcapsules are ruptured by various means to release the material contained therein. In addition to release of physically observable materials such as ink in order to form a visible image, other types of active ingredients such as odor releasing materials, bacteriostatic materials, chemically active materials and the like have been provided in this manner.

SUMMARY OF THE INVENTION

The present invention relates to a new article containing ruptureable microcapsules. The novel article comprises two surfaces, sheets or opposed faces of a folded single sheet of coated paper which are temporarily bonded by means of an adhesive with ruptureable microcapsules dispersed therein. The microcapsules are ruptured by pulling apart the sheets which causes the capsules to rupture and release the ingredients contained therein. By selecting the relative physical properties of the sheet, adhesive, capsules and the binding forces amongst them, a high rate of capsule rupturing can be obtained consistently.

DETAILED DESCRIPTION OF THE INVENTION

The present invention relates to an article comprising at least two surfaces, sheets or opposed faces of a folded single sheet temporarily secured by means of a adhesive layer having microcapsules dispersed therein. The sheet materials of the present invention comprise coated paper. Generally flexible sheets of paper are preferred. Coated paper is a conventional and standard item in commerce. It is generally a fibrous sheet having a pigment-bearing resinous coating on one or both surfaces. Usually the pigment provides a white, bone or ivory coloration to the sheet. Most generally pigments producing a white coloration are used. The binder used in the resinous coating is generally colorless and/or transparent. The binder is generally a synthetic or natural organic polymeric material. Typical pigments for producing white coated paper are fine white pigment such as clay, calcium carbonate, titania, silica, zinc oxide, etc. Typical binders include latices (e.g., styrene-butadiene, butadiene-acrylonitrile, etc.), film-forming polymers (e.g., polymethylmethacrylate), and natural resins (e.g., casein, ammonium caseinate, starch, etc.). The coatings usually comprise between 65–90% by weight of pigment, preferably 70–80% by weight of pigment, and 10–35% by weight of binder, preferably 20–30% by weight of binder. Papers having both sides coated are preferred in the advertising trade.

The adhesive material for the capsules must form a bond to the coated surfaces of the sheets which is stronger than the cohesive strength of the adhesive with the capsules dispersed therein. Although it is generally desirable to have an adhesive, the absolute cohesive strength of which is less than its adhesive strength to the coated surface of the coated paper cover sheets, this is not essential. When capsules are included within the adhesive composition, the effective cohesive strength of the adhesive tends to be reduced. Adhesives, which by themselves would cause the sheets to be damaged during separation, can be used in combination with capsules in the practice of the present invention because of lowered effective cohesive strength. The capsules in the present invention may comprise any ruptureable capsule containing an active ingredient therein. The tensile rupture strength of the capsules must be such that the cohesive failure of the adhesive results in capsule breakage. It has also been found that the size of the capsules plays a role in the usefulness of capsules within ruptureable sheets according to the practice of the present invention. Generally the capsules should have an average diameter between 6 and 50 microns and preferably between 12 and 30 microns when the capsule payload is between 80 and 90% by weight of the total capsule weight. It is highly preferred that the capsules have an average diameter between 14 and 26 microns and it is most preferred that the capsules have a diameter between 15 and 25 microns. These dimensions play a surprisingly important role in the ability to control the percentage of rupture of capsules in the practice of the present invention. With lower payloads (e.g., 70–80%), the capsules should be larger to provide the necessary rupture strength. The broadest range of capsule size under any conditions would be about 4 to 80 microns, with 8 micron capsules used with a 90–95% by weight payload. Eight to thirty micron capsules are generally preferred.

A basic relationship exists amongst the factors of peel force, adhesive coating weight and the median capsule diameter. This relationship can be expressed as $P = k(C_w/d^2)$, wherein P equals the peel force, $C_w$ equals the adhesive line coating weight, d equals the median diameter of the capsules and k equals a co-efficient relating to binder and substrate properties. The peel force should be in the range of 1.5 to 12 ounces per lineal inch, preferably 1.5 to 8.0 ounces per lineal inch. The coating weight of adhesive and microcapsules should be at a coating weight of approximately one pound for 300 to 800 square feet. Preferably the coating weight should be between approximately one pound for each 400 to 650 square feet. At higher coating weights, the surface of the cover sheets tend to tear, while at lower coating weights, the sheets tend to pull apart and the adhesive to paper bond tends to rupture in advance of the capsules included therein. The capsules should form between 20 and 90 percent by volume of the total adhesive composition, and preferably between 50 and 85 percent of the total composition volume. If certain microcapsule shell materials are used, such as gelatin, the capsule may comprise as much 100% of the adhesive compositions.

Even with these considerations being met, the coated surfaces of coated paper could not be used successfully as the adhesively bonded surface in the manufacture of two faces or sheets bearing releasable microencapsulated materials between them. It was found that the bond of the conventional adhesives to the coating on the paper and the distribution of the adhesive was not uniform. The adhesive bond between the paper coating and the capsule-bearing adhesive would fail before the cohesive strength of the capsule-bearing adhesive would, fibers would either be pulled from the paper or adhesive would fail without rupture of large percentages of capsules. It was difficult to satisfactorily adhere the capsule-bearing adhesive to the coated paper surface, with irregular appearance and non-uniform bond strength developing. Additionally, the adhesive tended to soak into the paper, causing microcapsules to be insufficiently bonded to the surface or the bond between the sheets to be too weak.

The present invention enables the manufacture of a device for exposing a liquid (e.g., to the atmosphere), said device comprising:
(1) at least two surfaces of coated paper bound by an adhesive composition layer,
(2) said adhesive composition layer containing microcapsules with said liquid within the shell of said microcapsules, and
(3) said microcapsules having an average diameter between 4 and 80 micrometers, the cohesive strength of the adhesive composition layer being less than the strength of the bond between said adhesive composition and a coated face of said sheets, the tensile rupture strength of said microcapsules being less than the cohesive strength of the adhesive composition, and the rupture force of said adhesive composition layer containing microcapsules at 50% relative humidity being between at least 2 ounces per linear five-and-one-half inches and less than 45 ounces per linear five-and-one-half inches (greater than 4.0 g/cm and less than 90 g/cm). It is preferred that the rupture strength between the sheets excedes 8.0 g/cm and is less than 80 g/cm and most preferably excedes 16 g/cm and is less than 75 g/cm. The minimum strength at this ambient condition (i.e., 20° C. and 50% R.H.) is necessary to keep the sheets from falling apart from forces incurred during handling. This problem has frequently occurred in magazine inserts where coated paper was used. The maximum limit on the rupture strength is necessary to keep the paper from tearing (termed fiber pull or fiber rupture) before the adhesive an capsules rupture. This would prevent release of the liquid from the capsules.

It is also desirable to have the construction resist the effects of variable ambient conditions. Certain products presently used on uncoated paper stock work in ambient conditions but fail in transit or on storage as the temperature and humidity change. Given the fact that some of these compositions fail at even standard conditions (20° C. and 50% R.H.), they tend to fail worse at more extreme conditions such as 30° C. and 80% R.H. or on dry conditions. For example, some binders or capsules are dehydrated by storage in heated warehouses during the winter and become so fragile that simple handling will rupture them. Complaints have been made by purchasers of magazines that all of the various odors in inserts are being released prior to usage of the magazine. The entire magazine tends to have a strong composite odor of many scents rather than being able to provide distinct individual scents. It is therefore desirable that rupture strength excede 4.0 g/cm after storage at 120° C. and less than 1% R.H. for seventy-two hours. This test would be performed by storage in an oven, removal to a neutral environment (e.g., sealed bag or jar) until the article is at room temperature, and then measuring the rupture strength. It is preferred that the rupture strength is at least 8.0 g/cm and most preferred that the rupture strength is at least 16 g/cm under those conditions. The article must still display a rupture strength between 4 and 90 g/cm at 20° C. and 50% R.H.

A number of methods have been found which enable these conditions to be met according to the present invention. The use of viscosity increasing agents in the binder provides a more even coating and one that ruptures before fiber pull begins. The use of additional coatings over the coated paper which contain polymers different from the binder of the adhesive layer and which do not form a solution or chemically bond to the binder of the adhesive layer provides a useful article according to the present invention. The use of larger size capsules tends to weaken the cohesive strength of the adhesive composite and prevent fiber pull. The use of capsules which are not moisture sensitive in combination with these large capsules (i.e., greater than 30 microns and up to 95 microns) provides a useful adhesive layer. Higher capsule-to-binder ratios reduce the cohesive strength of the adhesive, as does the addition of non-viscosity enhancing particulate fillers.

According to the present invention, it has been found that the preferred method of the addition of viscosity increasers (viscofiers), for reasons unknown, solved all of the above-identified problems in the use of coated paper base. The use of viscofiers also reduced the criticality of proportions of materials and provided increased coating and manufacturing latitude. Viscosity enhancers or viscosity increasing agents are well known in the art. Any material which when present in the coating solution in an amount not greater than 10% by weight increases the viscosity by at least 5% is a viscofier according to the present invention. Preferably viscosity is increased by at least 20%. They are either inorganic particulate materials (e.g., silica, amorphous silica, bentonite clay, montmorillonite clay, etc.) or organic particulate or soluble materials (e.g., water softenable acrylic particles, water swellable poly(methylmethacrylate), water soluble or organic solvent soluble polymers, etc.). The inorganic particles tend to be preferred. The viscofiers enhancers have been found to be necessary in dry weight proportions of the adhesive mix in amounts of from 0.25 to 12% by weight, preferably from 5 to 12% by weight. In general, the weight proportions of materials in the dried adhesive layers according to the present invention are generally as follows:

Microcapsules: 21–80%
Adhesive: 19.75–70%
Viscosity Enhancers: 0.25–12%

Other optional ingredients such as surfactants, coating aids and the like may be present. Preferred proportions of these ingredients are:

Microcapsules: 44.5–80%
Adhesive: 19.5–55%
Viscosity Enhancers: 0.5–10%

The ability to use coated paper in the manufacture of these articles is important because that material is the standard printing medium of the trade. Those papers enable the highest quality printings to be made in combination with the releasable materials of the present invention.

The nature and composition of the adhesive binder is not critical to the practice of the invention as long as the required adhesive and cohesive properties are met. The adhesive may be pressure sensitive, water or solvent soluble or thermally activatable. A single layer of a non-pressure-sensitive adhesive is preferred. There is no need for rejoining the sheets after rupturing of the capsules and so the pressure sensitive function is not necessary.

The adhesive (with microcapsules) may be applied between two separate sheets in either a continuous or discontinuous patterns. It is usually desirable to leave at least some portion of at least one outer edge of the sheets unbonded so as to provide an area where separation can be easily started. A single sheet may be folded so as to form two facing sheets joined along one edge. The adhesive may be applied on the interior area adjacent the fold. This provides a folded article that can be readily opened, rupturing the capsules, yet leaves a single artifact rather than two sheets after use.

It is preferred that the capsule-bearing adhesive coated inside portion of the single sheets (e.g., from the fold to the end of the adhesive) constitute from 5 to 40% of the surface area of the sheets. In two sheet constructions, 10 to 95 percent adhesive coverage is used. Some uses may allow for only a single corner to be uncoated so as to provide a starting point for the separation of the sheets, but the 5 to 40% range is preferred with 10 to 30% more preferred in two sheet constructions.

Any class of adhesives including but not limited to polyurethanes, polyacrylates, polyvinyl resins (e.g., polyvinyl alcohol, polyvinyl chloride), polyamides, polyesters, polyolefins, starches, gum arabic, gelatin and the like may be readily used in the practice of the present invention. Washing of the capsules before mixing them with the adhesive tends to provide more consistency in their properties by removing low molecular weight, unreacted materials.

In effect, to best practice the present invention it is desirable that certain properties within the article have relative values for each of the materials used. The cohesive strength of the sheet material should exceed the adhesive strength between the binder and the sheet. The adhesive strength of the binder to the sheet should exceed the cohesive strength of the binder and capsules therein. The cohesive strength of the binder should exceed the tensile rupture limits of the capsules.

As previously noted, the size of the capsules has an important effect upon the practice of the present invention. With capsules less than 8 microns, there tends to be less rupturing of the capsules as to prevent the useful and efficient release of materials. Above 30 microns, the particles are so large that they are more readily burst by handling of the sheets and manufacturing procedures. Furthermore, with the large size particles it is extremely difficult to control bursting upon separation of the sheets because of increased effects upon adhesive and cohesive properties of materials in contact with the capsules. The preferred ranges of 8 to 30 and 15 to 25 microns is important to the practice of the present invention. Within these limits, rupture in excess of 50 percent of the capsules can be easily obtained. Rupture in excess of 80 percent of the capsules can often be accomplished in the practice of the present invention within those limits.

The capsules may contain a wide variety of active materials therein. The least useful of materials to be included therein would be coloring agents since separation of the sheets would generally produce uniform coloration rather than a distinct image. The most preferred types of ingredients would be fragrant materials (such as essences and perfumes) or materials which provide chemically active vapors or liquids (e.g., bacteriostats or deodorants) to be wiped on or transferred to another surface. These may or may not also be colored. For example, a testing kit for the presence of chemical vapors could be produced by providing material within the capsules which would react in the vapor phase with the material for which a leak is being investigated. By separating the sheet, rupturing the capsules and exposing the vapor test material, a color forming reaction in the air or on the sheet could be readily observable. Another particularly useful format would be to include the microcapsules within a water-remoistenable adhesive and to use the mixture as the binding adhesive for novelty envelopes. For example, the microcapsules could contain the aromatic essence of baby oil, cake or pizza for invitation envelopes for a baby shower, wedding (or birthday party), or general party, respectively. The sides of the sheets with the capsule-bearing adhesive thereon are preferably printed under the adhesive or adjacent the adhesive.

This invention may be practiced with a number of various modifications that provide new and useful articles and processes. For example, the adhesive composition with capsules may be associated with various printed formats to form novelty items. The exterior sheets or exposed inner face of the sheets may have questions or stories or rhymes, and under the adhesive may be a printed picture answering the question, depicting the story or completing the rhyme, with the released fragrance emphasizing the picture further.

The capsule bearing adhesive layer in the construction of the present invention may also be used for a security device. In an article such as a coupon, lottery ticket or gaming card, the important display could be located under the adhesive. Once the article had been opened and the fragrance released, any subsequent recipient would be aware of its prior use and could be apprised of the possibility of tampering. The adhesive being non-pressure sensitive, it is not repositionable, the sheets are not easily rebonded, and there would be no release of fragrance if the sheets were robonded with additional non-fragranced adhesive and reopened. The absence of reduced level of fragrance would indicate that the article had been tampered with.

These and other aspects of the present invention will be shown in the following examples.

EXAMPLE 1

An oil having the aroma of roses was encapsulated in a urea-formaldehyde resin made according to the process of Example 20 of U.S. Pat. No. 3,516,941. The capsules had an average diameter of about 17 micrometers and an estimated payload of 85% by weight (ratio of oil to total capsule weight).

A coating formulation was prepared comprising 58.30 parts capsules, 31.90 parts polyvinyl alcohol, 0.9 parts glycerine (plasticizer) and 8.90 parts Syloid® amorphous silica viscosity enhancer in a water slurry. This formulation was coated at 3.0 lbs. per 1300 sq. ft. (dry weight) onto double-side coated paper base stock. The coating was made in a stripe down the middle of the paper and the paper folded sharply around the stripe after coating. The coated and folded paper was air dried at ambient conditions for two days.

Sections of the coated paper were cut to provide a folded sheet with a 20% portion of the paper extending from the fold coated with adhesive and capsules. The edges of the sheets were grasped by hand and pulled open sharply. There was a burst of rose aroma after the interior adhesive strip was ruptured.

The same composition, without the addition of the amorphous silica provided a functional article but of much poorer quality. The adhesive coating was uneven, microcapsule agglomerated, and a lower percentage of capsules were therefore ruptured during use.

EXAMPLES 2-3

Example 1 was twice repeated, replacing the silica viscofier with equal weight amoutns of (1) a water soluble carboxyvinyl polymer viscofier (Carbopol 691) and (2) sodium alginate, a water soluble viscofier. The coatings appeared smooth and uniform. Upon separation of the adhesively secured faces, a high percentage of the capsules were ruptured.

EXAMPLES 4-9

Example 1 was repeated without the use of the viscosity enhancing agent. The rupture strength of the adhesive then exceded 45 g/cm and the paper was torn without significant rupture of the adhesive and capsules.

The same adhesive composition was then used on five sheets of coated paper which were first primed with five different precoats, (1) high molecular weight poly(vinyl alcohol), (2) low molecular weight poly(vinyl alcohol), (3) poly(vinyl pyrrolidone), (4) an acrylic resin, and (5) a polyurethane resin. The first four coatings blended with the adhesive coating or chemically bonded thereto, raising the rupture strength to more than 45 g/cm. Only the polyurethane coating which neither bonded nor dissolved in the adhesive binder provided a useful coating. The bond strength was about 4 g/cm with that coating at 20° C. and 50% R.H.

EXAMPLE 10

The binder composition of Example 1 without the viscosity enhancing agent was used with 85 micron capsules instead of the 20 micron capsules. This coating worked well, but was not preferred because the large capsules could be broken during handling without rupture of the adhesive. The bond strength to the coated paper was between 30 and 50 g/cm.

EXAMPLE 11

The binder composition of Example 1 without the viscosity enhancing agent was used with 20 micron capsules having an 88% payload instead of an 85% payload. This was done by using less resin during the formation of the microcapsules and produced a thinner shell article (hence a greater payload). The thinner shell produced a weaker capsule, and therefore a weaker adhesive. The rupture strength was still in the high end of the acceptable range at about 80 g/cm.

EXAMPLE 12

The binder composition of Example 1 without the viscosity enhancing agent was used with the capsules of that example and additionally 5% by dry weight of 25 micron silica particles. These particles reduced the cohesive strength of the adhesive layer to about 40 g/cm.

We claim:

1. A device for exposing a liquid, said device comprising
   (1) at least two surfaces of coated paper bound by an adhesive composition layer,
   (2) said adhesive composition layer containing microcapsules with said liquid within the shell of the microcapsules, and
   (3) said microcapsules having an average diameter between 4 and 80 micrometers,
   the cohesive strength of the adhesive composition layer being less than the strength of the bond between said adhesive composition and a coated face of said sheets, the tensile rupture strength of said microcapsules being such that the cohesive failure of the adhesive results in breakage of the microcapsules, and the tensile rupture strength between said two surfaces being at least 4.0 g/cm and less than 90 g/cm at 20° C. and 50% relative humidity and greater than 4.0 g/cm after storage at 120° C. and less than 1% relative humidity for seventy-two hours.

2. The device of claim 1 wherein said adhesive composition comprises said microcapsules and a viscofier.

3. The device of claim 2 wherein said surfaces are on flexible sheets of coated paper and said viscofier comprise from 0.25 to 12% by dry weight of said adhesive composition layer.

4. The device of claim 3 wherein said microcapsules have an average diameter between 14 and 26 micrometers.

5. The device of claim 4 wherein said microcapsules comprise between 50 and 85% by volume of said adhesive composition.

6. The device of claim 3 wherein said liquid is an odor releasing material.

7. The device of claim 2 wherein said microcapsules have an average diameter between 12 and 30 micrometers.

8. The device of claim 7 wherein said liquid is an odor releasing material.

9. The device of claim 2 wherein said microcapsules comprise gelatin and are between 21 and 100% by weight of said adhesive composition, said binder comprises between 0 and 78.75% by weight and said viscofier comprises between 0.25 and 12% by weight.

10. The device of claim 9 wherein said liquid is an odor releasing material.

11. The device of claim 2 wherein said liquid is an odor releasing material.

12. The device of claim 2 wherein said adhesive is a water-remoistenable adhesive.

13. The device of claim 1 wherein said microcapsules have an average diameter between 8 and 30 micrometers.

14. The device of claim 13 wherein said microcapsules comprise between 50 and 85% by volume of adhesive composition.

15. The device of claim 1 wherein said microcapsules comprise between 50 and 85% by volume of said adhesive composition.

16. The device of claim 1 wherein said liquid is an odor releasing material and the shell of said microcapsule comprises a urea-formaldehyde resin.

17. The device of claim 1 wherein said liquid is an odor releasing material.

18. The device of claim 1 wherein a polymeric coating is present over said coated paper surface which is not dissolved by or chemically bonded to said adhesive composition.

19. The device of claim 1 wherein said adhesive composition contains said microcapsule and a non-viscosity enhancing particulate filler.

20. A device for exposing a liquid, said device consisting essentially of
(1) two surfaces of paper, at least one of which surfaces is a surface of coated paper, said surfaces being bound by an adhesive composition layer, said coated paper comprising paper which is coated with a resinous binder and white, bone or ivory pigment, and said at least one surface of coated paper having a printed image thereon,
(2) said adhesive composition layer containing microcapsules with said liquid within the shell of the microcapsules, and
(3) said microcapsules having an average diameter between 4 and 80 micrometers,
the cohesive strength of the adhesive composition layer being less than the strength of the bond between said adhesive composition and a coated face of said sheets, the tensile rupture strength of said microcapsules being such that the cohesive failure of the adhesive results in breakage of the microcapsules, and the tensile rupture strength between said two surfaces being at least 4.0 g/cm and less than 90 g/cm at 20° C. and 50% relative humidity.

21. A device for exposing a liquid, said device comprising
(1) at least two surfaces of coated paper bound by an adhesive composition layer,
(2) said adhesive composition layer containing microcapsules with said liquid within the shell of the microcapsules, and
(3) said microcapsules having an average diameter between 4 and 80 micrometers,
the cohesive strength of the adhesive composition layer being less than the strength of the bond between said adhesive composition and a coated face of said sheets, the tensile rupture strength of said microcapsules being such that the cohesive failure of the adhesive results in breakage of the microcapsules, and the tensile rupture strength between said two surfaces being at least 8.0 g/cm and less than 90 g/cm at 20° C. and 50% relative humidity and greater than 4.0 g/cm after storage for seventy-two hours at 120° C. and less than 1% relative humidity.

22. The device of claim 21 wherein said tensile rupture strength between said two surfaces is at least 16.0 g/cm and less than 90 g/cm at 20° C. and 50% relative humidity.

23. The device of claim 22 wherein said liquid is an odor releasing material.

24. The device of claim 22 wherein said tensile rupture strength is at least 8.0 g after storage for seventy-two hours at 1% relative humidity and 120° C.

25. The device of claim 21 wherein said liquid is an odor releasing material.

26. The device of claim 25 wherein said tensile rupture strength is at least 8.0 g after storage for seventy-two hours at 1% relative humidity and 120° C.

27. The device of claim 21 wherein said tensile rupture strength is at least 8.0 g after storage for seventy-two hours at 1% relative humidity and 120° C.

* * * * *